US00PP17551P2

(12) United States Plant Patent
Probst

(10) Patent No.: US PP17,551 P2
(45) Date of Patent: Apr. 3, 2007

(54) ***PHLOX* PLANT NAMED 'FLOWER POWER'**

(50) Latin Name: *Phlox maculata*
Varietal Denomination: Flower Power

(76) Inventor: Darrell R. Probst, 63 Williamsville Rd., Hubbardston, MA (US) 01452-1315

( * ) Notice: Subject to any disclaimer, the term of this patent is extended or adjusted under 35 U.S.C. 154(b) by 0 days.

(21) Appl. No.: 11/049,219

(22) Filed: Feb. 1, 2005

(51) Int. Cl.
*A01H 5/00* (2006.01)

(52) U.S. Cl. ..... Plt./320
(58) Field of Classification Search ..... Plt./320
See application file for complete search history.

*Primary Examiner*—Anne Marie Grunberg
*Assistant Examiner*—Georgia Helmer
(74) *Attorney, Agent, or Firm*—C. A. Whealy

(57) ABSTRACT

A new and distinct cultivar of *Phlox* plant named 'Flower Power', characterized by its upright and compact plant habit; freely branching habit; large inflorescences with numerous white-colored flowers with a pink blush; and good garden performance.

1 Drawing Sheet

Botanical designation: *Phlox maculata.*
Cultivar denomination: 'Flower Power'.

BACKGROUND OF THE INVENTION

The present Invention relates to a new and distinct cultivar of *Phlox* plant, botanically known as *Phlox maculata,* and hereinafter referred to by the cultivar name Flower Power.

The new *Phlox* is a product of a planned breeding program conducted by the Inventor in Hubbardston, Mass. The objective of the breeding program was to create new compact *Phlox* cultivars with attractive flower coloration.

The new *Phlox* originated from an open-pollination in 1996 in Hubbardston, Mass. of the *Phlox maculata* cultivar Omega, not patented, as the female, or seed, parent with an unknown selection of *Phlox maculata,* as the male, or pollen, parent. The new *Phlox* was discovered and selected by the Inventor as a flowering plant within the progeny of the stated open-pollination in a controlled environment in Hubbardston, Mass. in 1996.

Asexual reproduction of the new cultivar by terminal cuttings at Hubbardston, Mass. since 1997, has shown that the unique features of this new *Phlox* are stable and reproduced true to type in successive generations.

SUMMARY OF THE INVENTION

Plants of the cultivar Flower Power have not been observed under all possible environmental conditions. The phenotype may vary somewhat with variations in environment such as temperature and light level without, however, any variance in genotype.

The following traits have been repeatedly observed and are determined to be the unique characteristics of 'Flower Power'. These characteristics in combination distinguish 'Flower Power' as a new and distinct cultivar of *Phlox:*

1. Upright and compact plant habit.
2. Freely branching habit.
3. Large inflorescences with numerous white-colored flowers with a pink blush.
4. Good garden performance.

Plants of the new *Phlox* can be compared to plants of the female parent, the cultivar Omega. In side-by-side comparisons conducted in Hubbardston, Mass. plants of the new *Phlox* differed from plants of the cultivar Omega in the following characteristics:

1. Plants of the new *Phlox* had longer and narrower inflorescences than plants of the cultivar Omega.
2. Plants of the new *Phlox* and the cultivar Omega differed in flower coloration as plants of the cultivar Omega had white-colored flowers with small pink-colored centers.

Plants of the new *Phlox* can be compared to the *Phlox* cultivar Indico, disclosed in U.S. Plant Pat. No. 15,389. In side-by-side comparisons conducted in Hubbardston, Mass., plants of the new *Phlox* differed from plants of the cultivar Indico in the following characteristics:

1. Plants of the new *Phlox* were much more compact than plants of the cultivar Indico.
2. Plants of the new *Phlox* had shorter internodes than plants of the cultivar Indico.
3. Plants of the new *Phlox* and the cultivar Indico differed in flower color as plants of the cultivar Indico had solid white-colored flowers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which more accurately describe the actual colors of the new *Phlox.* The photograph comprises a side perspective view of a typical flowering plant of 'Flower Power'.

DETAILED BOTANICAL DESCRIPTION

The aforementioned photograph, following observations and measurements describe plants grown in Pennsylvania in a polyethylene-covered greenhouse and under commercial production practices. Plants were grown in gallon containers and were about five months old when the photograph and description were taken. During the production of the plants, day temperatures ranged from 21 to 46° C. and night temperatures ranged from 18 to 29° C. In the following description, color references are made to The Royal Horticultural Society Colour Chart, 1995 Edition, except where general terms of ordinary dictionary significance are used.

Botanical classification: *Phlox maculata* cultivar Flower Power.

Parentage: Open-pollination of the *Phlox maculata* cultivar Omega, not patented, as the female, or seed, parent with an unknown selection of *Phlox maculata,* as the male, or pollen, parent.

Propagation:

*Type.*—By cuttings.

*Time to initiate roots, summer.*—About five days at 29° C.

*Time to initiate roots, winter.*—About three weeks at 21° C.

*Time to produce a rooted plant, summer.*—About 18 days at 29° C.

*Time to produce a rooted plant, winter.*—About four weeks at 29° C.

*Root description.*—Fine; white in color.

*Rooting habit.*—Freely branching.

Plant description:

*Plant form/habit.*—Upright and compact plant habit; columnar form; moderately vigorous growth habit. Freely branching habit, about six lateral branches per plant.

*Plant height.*—About 35 cm.

*Plant width* (*spread*).—About 18 cm.

*Lateral branches.*—Length: About 27 cm. Diameter: About 3 mm. Internode length: About 1.1 cm. Strength: Strong. Texture: Older stems, smooth, glabrous; young stems with sparse pubescence. Color: 146A overlain with close to 187A.

*Foliage description.*—Arrangement: Alternate, simple; sessile. Length: About 5.1 cm. Width: About 1.1 cm. Shape: Lanceolate. Apex: Acute to acuminate. Base: Attenuate. Margin: Entire. Texture, upper and lower surfaces: Sparsely pubescent. Venation pattern: Pinnate. Color: Developing and fully expanded leaves, upper surface: Close to 147A; venation, similar to lamina. Developing and fully expanded leaves, lower surface: Close to 147B; venation, similar to lamina.

Flower description:

*Flower type/habit.*—Single, rounded salverform flowers arranged in large panicles; flowers pinwheel in shape with imbricate petals. Flowers face upright and outward. Freely flowering habit; one inflorescence per lateral branch; each inflorescence with about 13 clusters of flowers with eight flowers per cluster.

*Fragrance.*—Faint; sweet and fresh.

*Natural flowering season.*—Continuously flowering throughout the summer in Pennsylvania. Flowers persistent.

*Postproduction longevity.*—Flowers last about seven to ten days on the plant.

*Inflorescence height.*—About 8 cm.

*Inflorescence diameter.*—About 4.75 cm.

*Flower buds.*—Height: About 1.8 cm. Diameter: About 3.5 mm. Shape: Elongated oblong. Color: Towards the base, close to 145D; towards the apex, close to 155D.

*Flowers.*—Diameter: About 2 cm. Depth: About 2.5 cm. Throat diameter: About 3 mm. Tube length: About 2.3 cm. Tube diameter, base: About 1.75 mm.

*Petals.*—Quantity per flower: Typically five in a single whorl; petals imbricate; petals fused at the base into a narrow tube. Lobe length: About 9 mm. Lobe width: About 1.1 cm. Shape: Roughly spatulate. Apex: Broadly acute. Margin: Entire. Aspect: Mostly flat. Texture, upper and lower surfaces: Smooth, glabrous; velvety. Color: Developing and fully expanded petals, upper surface: Close to 155D blushed with close to 61A. Developing and fully expanded petals, lower surface: Close to 155D blushed with close to 61B.

*Sepals.*—Quantity per flower: Typically five in a single whorl, fused; narrow tubular calyx. Length: About 8 mm. Width: About 2 mm. Shape: Lanceolate. Apex: Acuminate. Texture, upper and lower surfaces: Smooth, glabrous. Color, upper and lower surfaces: Close to 144A.

*Peduncles.*—Length: About 5 mm. Diameter: About 1.5 mm. Angle: About 50 to 60° from vertical. Texture: Pubescent. Color: Close to 144A.

*Pedicels.*—Length: About 2 mm. Diameter: About 1 mm. Angle: About 0 to 30° from vertical. Texture: Pubescent. Color: Close to 144A.

*Reproductive organs.*—Stamens: Quantity per flower: Typically five. Anther shape: Linear, elongated. Anther length: About 2 mm. Anther diameter: Less than 1 mm. Anther color: Close to 15A. Pollen amount: Moderate. Pollen color: Close to 15A. Pistils: Quantity per flower: Typically one. Pistil length: About 2.1 cm. Stigma shape: Tri-parted. Stigma color: Close to 9A. Style length: About 1.9 cm. Style color: Close to 145C. Ovary color: Close to 144A.

*Seed/fruit.*—Seed and fruit development have not been observed.

Disease/pest resistance: Plants of the new *Phlox* have been observed to be somewhat resistant to Powdery Mildew. Plants of the new *Phlox* have not been noted to be resistant to pests and other pathogens common to *Phlox.*

Garden performance: Plants of the new *Phlox* have been observed to have good garden performance and tolerate rain, wind and tolerated temperatures from −28 to 46° C.

It is claimed:

1. A new and distinct cultivar of *Phlox* plant named 'Flower Power', as illustrated and described.

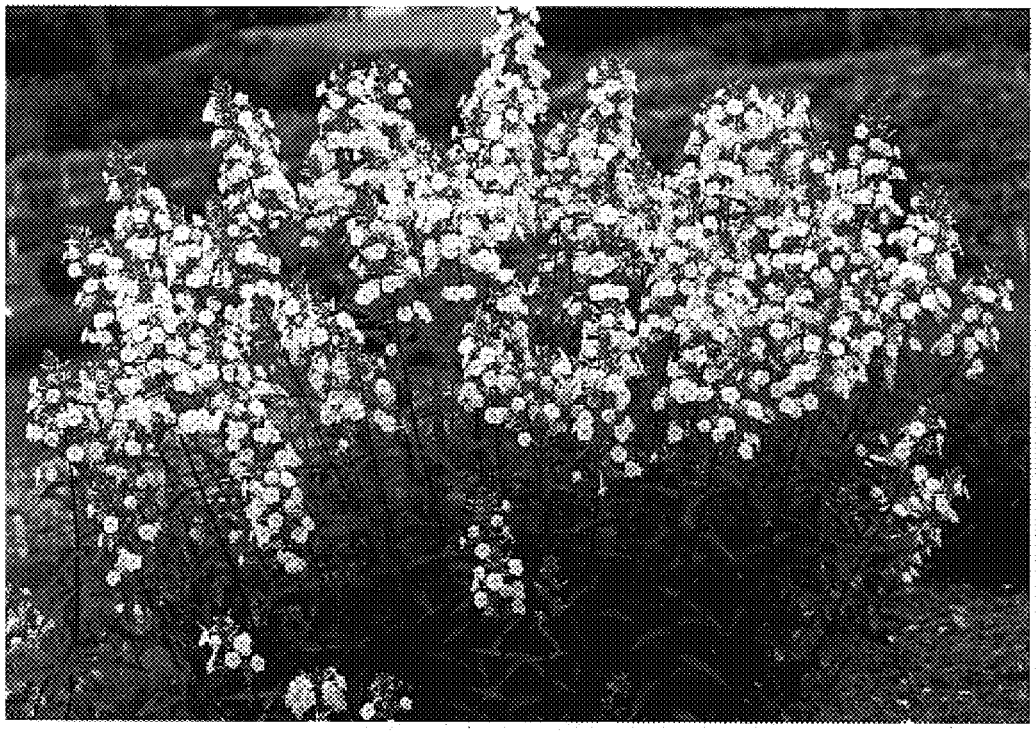

* * * * *